(12) United States Patent
Bollenbeck et al.

(10) Patent No.: US 8,866,482 B2
(45) Date of Patent: Oct. 21, 2014

(54) PREPROCESSING CIRCUIT FOR RECEIVE SIGNALS OF A LOCAL COIL

(75) Inventors: Jan Bollenbeck, Eggolsheim (DE); Ralph Oppelt, Uttenreuth (DE)

(73) Assignee: Siemens Aktiengesellschaft, München (DE)

( * ) Notice: Subject to any disclaimer, the term of this patent is extended or adjusted under 35 U.S.C. 154(b) by 497 days.

(21) Appl. No.: 13/183,065

(22) Filed: Jul. 14, 2011

(65) Prior Publication Data

US 2012/0020259 A1 Jan. 26, 2012

(30) Foreign Application Priority Data

Jul. 20, 2010 (DE) .......................... 10 2010 027 672

(51) Int. Cl.
*G01V 3/00* (2006.01)
*G01R 33/36* (2006.01)
*A61B 5/055* (2006.01)

(52) U.S. Cl.
CPC ............ *G01R 33/3621* (2013.01); *A61B 5/055* (2013.01)
USPC .......................................... 324/322; 324/318

(58) Field of Classification Search
USPC ................... 324/322, 318, 314, 300
See application file for complete search history.

(56) References Cited

U.S. PATENT DOCUMENTS

| 4,777,438 A | 10/1988 | Holland |
| 6,297,637 B1 * | 10/2001 | Feld et al. ...................... 324/322 |
| 7,834,628 B2 * | 11/2010 | Biber et al. .................... 324/318 |
| 8,379,549 B2 * | 2/2013 | Oppelt et al. .................. 370/297 |
| 8,384,388 B2 * | 2/2013 | Biber ............................. 324/322 |
| 8,390,292 B2 * | 3/2013 | Bollenbeck ................... 324/322 |

FOREIGN PATENT DOCUMENTS

| CN | 1455265 A | 11/2003 |
| CN | 101581771 A | 11/2009 |
| DE | 10 2008 023 467 A1 | 12/2009 |

OTHER PUBLICATIONS

German Office Action dated Jun. 8, 2011 for corresponding German Patent Application No. DE 10 2010 027 672.3 with English translation.
Chinese Office Action cited in CN2011102017624, mailed Jun. 5, 2014.

* cited by examiner

*Primary Examiner* — Louis Arana
(74) *Attorney, Agent, or Firm* — Lempia Summerfield Katz LLC

(57) ABSTRACT

A preprocessing circuit for receive signals of a local coil in a magnetic resonance facility (1) includes an arrangement for supplying at least one auxiliary frequency signal of an auxiliary frequency. For at least one or the auxiliary frequency signal, a frequency multiplier generates the auxiliary frequency signal from an intermediate signal transmitted from a receive system of the magnetic resonance facility by way of a transmission link. The multiplier generates the auxiliary frequency signal with a frequency corresponding to a whole-number fraction of the auxiliary frequency.

22 Claims, 3 Drawing Sheets

PREPROCESSING CIRCUIT FOR RECEIVE SIGNALS OF A LOCAL COIL

This application claims the benefit of DE 10 2010 027 672.3, filed Jul. 20, 2010.

BACKGROUND

The present embodiments relate to a preprocessing circuit for receive signals of a local coil for a magnetic resonance (MR) facility. Proposals have been made to undertake part of processing of receive signals in or at least in the region of a local coil for magnetic resonance circuits.

Local coils are increasingly used in magnetic resonance circuits to record magnetic resonance images with a high signal-to-noise ratio. The excited nuclei in the object to be recorded induce a voltage in the coil conductor of the local coil. The voltage generally is amplified using a low-noise amplifier (LNA) and then forwarded by cable connection at the magnetic resonance frequency (transmit frequency) to an input of a receiver of the receive system. To improve the signal-to-noise ratio further even with high-resolution magnetic resonance images, high-field systems are used. The basic field strengths of a high-field system are around three Tesla or higher.

Local coils are generally connected to a patient couch by way of suitable plug-in points. Because the patient couch may be moved around, cable connections meters long are frequently used to forward the received signals to the receive system. Local coils may include a number of individual coil elements (loops), each supplying a receive signal, so that wired transmission links are generally required for each of these so-called receive channels.

An arrangement for transmitting magnetic resonance signals received with the aid of local coils is known from DE 10 2008 023 467 A1. It is proposed there in one embodiment that two receive signals are transmitted, in other words multiplexed (frequency multiplexing), by way of a single connecting line. It is also proposed there that low intermediate frequencies may be used to transmit the receive signals. The intermediate frequencies are selected so that the intermediate freqeuncies are located symmetrically around the sampling frequency of the downstream analog/digital converter.

To convert the receive signals to the intermediate frequencies, a preprocessing circuit is provided. The preprocessing circuit includes at least a first mixer and at least a second mixer. The mixers operate as frequency converters and use two different auxiliary frequency signals (local oscillator signals). The auxiliary frequency signals are supplied to the preprocessing circuit by a coaxial cable. The coaxial cable also is used to transmit the receive signals (with an intermediate frequency) to a receiver of the receive system of the magnetic resonance facility. Therefore, one or more auxiliary frequency signals may be transmitted to the local coil on one coaxial cable and one or more magnetic resonance signals (each transformed to an intermediate frequency) may be transmitted away from the local coil.

The requirements specified for the transmission link from the point of view of auxiliary frequency signal processing are less stringent than the requirements resulting from the point of view of intermediate frequency signal processing. At the feed point, line attenuation may largely be compensated for by increasing the feed power. However, as the frequency of the auxiliary frequency signal increases, more and more problems may result due to motion- and/or time- and temperature-dependent phase responses and reflections (level uncertainties) caused by discontinuities (e.g., plug-type connectors).

In the example from DE 10 2008 023 467 A1, the required auxiliary frequency is calculated as the magnetic resonance frequency (transmit frequency) +/- the intermediate frequency. From auxiliary frequencies of around 150 MHz upwards, the described effects make it necessary to adjust the transmission link so that the advantages described by DE 10 2008 023 467 A1—thin and low-cost cable design, use of low-cost, for example non-coaxial plug-type connectors, narrowband design of switches to select certain coil elements—are increasingly negated.

If, for example, the receive system with its intermediate frequencies disposed with mirror symmetry in relation to a 10 MHz sampling rate as described in DE 10 2008 023 467 A1 is to be used for operation with a seven Tesla magnetic resonance system, an auxiliary frequency signal pair of 285 MHz and 305 MHz results. At such auxiliary frequencies, the advantages gained by using the intermediate frequencies may be lost again.

Other types of preprocessing may also be provided by a preprocessing circuit at the local coil. The other types of preprocessing may also use the transmission of auxiliary frequency signals.

SUMMARY AND DESCRIPTION

The present embodiments may obviate one or more of the drawbacks or limitations in the related art. For example, a high-frequency auxiliary frequency signal is supplied in a preprocessing circuit. A simple and low-cost embodiment of the cabled transmission link may still be realized.

A preprocessing circuit for receive signals of a local coil includes an arrangement for supplying at least one auxiliary frequency signal of an auxiliary frequency. For at least one or all of the auxiliary frequency signals, a frequency multiplier (e.g., a frequency doubler) generates the auxiliary frequency signal from an intermediate signal transmitted from a receive system of the magnetic resonance facility. The intermediate signal is tranmitted on a transmission link with a frequency corresponding to a whole-number fraction of the auxiliary frequency, such as half the auxiliary frequency. According to one embodiment, the processing circuit is extended to include a frequency multiplier, so that the auxiliary frequency signals are generated locally from a lower-frequency intermediate signal, which is supplied by way of a transmission link from the receive system. In many practical instances, a frequency doubler is provided, so that the intermediate signal has a frequency which is half the auxiliary frequency. The transmitted frequencies remain low in respect of the auxiliary frequency signals, so that simple (e.g., thin and low-cost) cable may be used. In high-field systems of, for example, around seven Tesla, in which local coils with a large number of coil elements, for example, 128 receive channels, are used, the arrangement may be useful since a large number of cables may be required. At the same time, the use of small and simple, for example, non-coaxial plug-type connectors, may be used. If an appropriate multiplication factor is selected, system components from systems with a lower basic field, for example, from three Tesla systems, may also be used in systems with a higher basic field, for example seven Tesla systems, without modification. Such system components are, for example, the couch cabling, a switching matrix for assigning receive channels to receiver inputs, local oscillators (synthesizers), intermediate frequency receivers and the like.

In one embodiment, the preprocessing circuit may also be used in the context of the frequency multiplexing according to DE 10 2008 023 467 A1. The problems primarily with magnetic resonance circuits with a high basic field may be eliminated by provision of the frequency multiplier.

In a further embodiment, a single wired transmission link is provided to transmit at least one receive signal and at least one intermediate signal. The wired transmission link, which may comprise at least one coaxial cable, is also used on a multiple basis. Embodiments are also possible, in which auxiliary frequency signals for example that are not to be multiplied but are to be used as transmitted, are transmitted by way of a transmission link used to transmit at least one receive signal, optionally in addition to at least one intermediate signal.

With multiple use of a transmission link, a multiplexer (e.g., a diplexer) may also be provided upstream of the frequency multiplier to separate the intermediate signal from the receive signal. The intermediate signal is then forwarded to the frequency multiplier, which generates the auxiliary frequency signal.

When transmitting a number of intermediate signals, a multiplexer may be provided downstream or preferably upstream of the frequency multiplier to separate the auxiliary frequency signals or the intermediate signals. If the frequency multiplier is connected upstream of the auxiliary frequency multiplexer, only one frequency multiplier is required as the frequency multiplier already operates on the basis of the combined intermediate signals. Since however unwanted intermodulation products may occur in this process, in particular when using a non-linear frequency multiplication stage, provision may be made for the multiplexer also to be configured to suppress these unwanted intermodulation products as well as for the spectral separation of the different intermediate signals.

Spectral separation of the signals already takes place in the low frequency position (i.e., in respect of the intermediate frequencies) may be preferred. In this instance, at least two frequency multipliers are used but the dynamic requirement for the frequency multiplier is advantageously reduced. Reduction may occur because the two-frequency signal has a greater peak power (PEP, peak envelope power) than the respective individual frequencies. Also interfering intermodulation products of the intermediate signals no longer occur in such an arrangement.

In one embodiment, the preprocessing circuit comprises at least one mixer, which transforms a receive signal to a low intermediate frequency using the auxiliary frequency. Transform is useful, for example, if the concept described in DE 10 2008 023 467 A1 is to be applied.

In one embodiment, the frequency multiplier may be a passive frequency multiplier, such as a diode multiplier. A passive frequency multiplier prevents electrical power additionally being consumed in the housing of the preprocessing circuit or, if part of the local coil, in the local coil housing.

Provision does not in principle have to be made for all intermediate signals to be multiplied in each instance in order to generate the auxiliary frequency signals directly therefrom. Arrangements are possible for example, in which only an intermediate signal is multiplied (e.g., doubled) by way of the frequency multiplier, in order then to be supplied to at least one mixer. The other input of the mixer is formed by an auxiliary frequency signal transmitted unmodified to the preprocessing circuit. The desired auxiliary frequency signal is then present at the output of the mixer. For example, two auxiliary frequency signals and one intermediate signal may also be used. An intermediate signal, the frequency of which is to be multiplied by way of the frequency multiplier and which is then supplied to a first or second mixer, is provided to generate a first and second ultimately desired auxiliary frequency signal. The other inputs of the mixers are supplied with the two transmitted auxiliary frequency signals. In this manner, the demultiplexing of the two transmitted auxiliary frequency signals that are not to be multiplied is also configured more simply as the corresponding combined signal may be passed first to a multiplexer for splitting before the individual auxiliary frequency signals are each passed to a mixer. If spectral separation is performed upstream of the mixer, it is technically simpler, as the relative frequency gap is larger. As with the connection of the multiplexer upstream of the frequency multiplier, the dynamic requirement for the mixer is less stringent. The frequency gap of the two transmitted auxiliary frequency signals that are not to be multiplied may be selected so that the frequency gap corresponds to the frequency gap of the ultimately desired auxiliary frequency signals generated by the mixer. This selection may be advantageous if the local oscillator is designed for the predetermined frequency gap. The dimensioning of the multiplexer (separating filter) is also simplified, as described.

In one embodiment, the preprocessing circuit may be configured as a separate circuit. The separate circuit may be connected for example between a coil plug and a plug-in point on a patient couch.

As well as the preprocessing circuit, one embodiment also relates to a local coil with a preprocessing circuit. In this embodiment, the preprocessing circuit is therefore a fixed part of a local coil and is in particular incorporated in the local coil housing. Any of the embodiments relating to the preprocessing circuit may apply in a similar manner to a local coil.

In another embodiment, a method for supplying at least one auxiliary frequency signal of an auxiliary frequency to a preprocessing circuit for receive signals assigned to a local coil for a magnetic resonance facility is provided. For at least one auxiliary frequency signal, such as all auxiliary frequency signals, an intermediate signal with a frequency corresponding to a whole-number fraction of the auxiliary frequency is transmitted by way of a transmission link from a receive system to the preprocessing circuit, and a frequency multiplier is used to generate the auxiliary frequency signal from the intermediate signal. The method is also based on the idea of first transmitting intermediate signals, the frequency of which is a fraction of the frequency of the actually desired auxiliary frequency signal, in order then to transform to the desired auxiliary frequency, in the preprocessing circuit, by a frequency multiplier. This method allows the advantages already discussed in respect of the preprocessing circuit to be achieved.

The intermediate signal may be generated in the receive system, such as by a local oscillator. The intermediate signal is therefore already generated at the frequency at which the signal is also to be transmitted later by way of the transmission link. Alternatively, a suitable electronic system may be used to transform the signal first to the lower frequency but this arrangement may be associated with a higher level of complexity.

The transmission link may be used both to transmit at least one intermediate signal and also at least one receive signal, such as at an intermediate frequency. Different multiplexers may then be used. Generally, provision may be made for at least one multiplexer to be used to split different signals transmitted by way of the transmission link. If intermediate signals are transmitted to generate a number of auxiliary frequency signals, the intermediate signals to be split before the frequency may be increased, since this permits the dynamic requirements for the frequency multiplier or mixer to be reduced and, in particular, no interfering intermodulation products occur.

The increase may be used when, in addition to at least one intermediate signal to be multiplied in the preprocessing circuit, two or more auxiliary frequency signals are transmitted by way of the transmission link. The signals are then later to be transformed to a higher frequency by a mixer by mixing with the auxiliary frequency signal generated from the intermediate signal. In order words, provision may be made for at least one further auxiliary frequency signal to be generated by mixing at least one auxiliary frequency signal generated by a frequency multiplier with another auxiliary frequency signal. A multiplexer (separating filter) may separate auxiliary frequency signals transmitted together for the mixer before mixing.

DETAILED DESCRIPTION OF THE DRAWINGS

Figure 1:
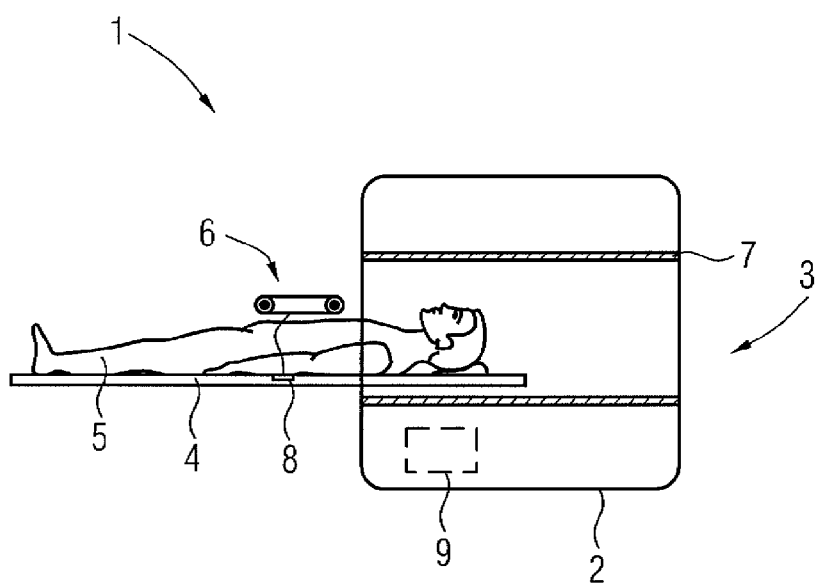
FIG. 1 shows a schematic diagram of one embodiment of a magnetic resonance facility.

FIG. 1 shows a basic outline of a magnetic resonance facility 1. The magnetic resonance facility 1 includes a magnet 2 with a patient space 3, into which a patient couch 4 on which the object to be imaged (e.g., a patient 5) may be introduced. Enclosing the entire patient space 3 is a whole-body coil 7, which may emit a signal that excites the nuclei in the patient 5 at a transmit frequency that is a function of the strength of the basic magnetic field. In one embodiment, the magnetic resonance facility 1 is a high-field system with a transmit frequency (also referred to as the magnetic resonance frequency) of 297.2 MHz. The values cited within the context of these exemplary embodiments are examples.

Figure 2:
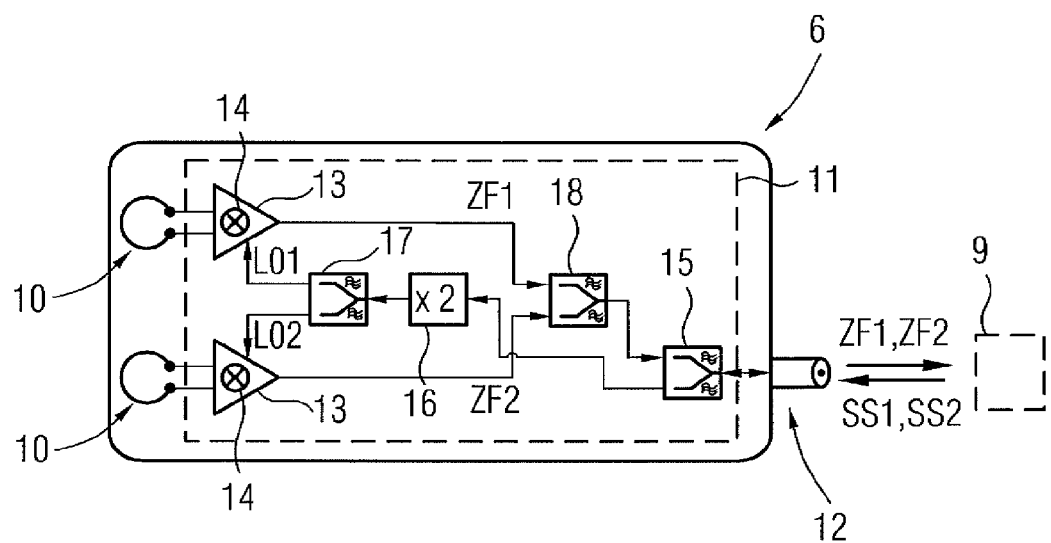
FIG. 2 shows a first exemplary embodiment of a local coil.

Receive signals (e.g., magnetic resonance signals) are to be received by a local coil 6 positioned on the patient 5. The local coil 6 may be connected by plug-in points 8 provided on the patient couch 4. The receive signals of the local coil 6 are to be transmitted by way of a transmission link to a receive system 9 of the magnetic resonance facility 1. Since meters of cable connections (e.g., meters of coaxial cable) are used, a simple and economic configuration is desired. Simple and economic configuration may be provided by permitting only low-frequency signals to be carried by the transmission link. FIG. 2 shows a basic outline of a first embodiment of a local coil 6. A number of individual coil elements (loops) 10, only two of which are shown here for purposes of simplicity, may initially be provided. Provision is also made for processing the received magnetic resonance signals at the same time within the local coil 6. To process the received signals, a preprocessing circuit 11 is disposed in the local coil housing. The receive signals of the two coil elements 10 shown are transformed to two different intermediate frequencies in the local coil 6. The transformation is to transmit two receive signals at the frequency by way of the wired transmission link 12 to the receive system 9. In order to generate these intermediate frequencies (ZF1, ZF2), two auxiliary frequency signals (LO1, LO2) are supplied. The auxiliary frequency signals (LO1, LO2) are used in the mixers 14 provided in a frequency-converting module 13 to transform the receive signals to the intermediate frequencies.

Provision is not made for supplying the auxiliary frequency signals LO1 and LO2 directly by way of the transmission link 12 from the receive system 9. To generate, for example, intermediate frequencies of 7.8 MHz and 12.2 MHz, which are both 2.2 MHz away from the system clock 10 MHz, auxiliary frequencies of 285 MHz and 305 MHz are used at the transmit frequency. Such frequences may require more expensive and more complex conversion of the transmission link 12.

In the exemplary embodiment shown in FIG. 2, two intermediate signals, referred to here as SS1 and SS2, are generated in the receive system 9. The frequency of the intermediate signals is half the required auxiliary frequencies, therefore an intermediate signal of 142.5 MHz and an intermediate signal of 152.5 MHz. The signals are transmitted by the transmission link 12, which is therefore used both for the intermediate signals and for the receive signals at the intermediate frequency, to the preprocessing circuit 11.

At the preprocessing circuit 11, the signals encounter a diplexer 15 (e.g., separating filter), which separates the receive signals at the intermediate frequency and the intermediate signals. The intermediate signals are then forwarded to a frequency multiplier 16, such as a frequency doubler. The multiplier 16 produces the auxiliary frequency signals LO1 and LO2 from the intermediate signals SS1 and SS2, which are then split with the aid of a further diplexer 17. The auxiliary frequency signals LO1 and LO2 are then each supplied separately to the mixers 14, so that the different intermediate frequencies ZF1 and ZF2 are generated.

The frequency-transformed receive signals are supplied to a diplexer 18, which combines the two receive signals at the intermediate frequencies and then forwards the combined signals by way of the diplexer 15 to the transmission link 12, where the combined signals may then be transmitted to the receive system 9.

In this embodiment, the LO diplexer 17 is used not only for the spectral separation of the two components but also for the suppression of unwanted intermodulation products, which are generated in the non-linear doubler stage (frequency doubler 16) from the two intermediate signals SS1, SS2.

Figure 3:
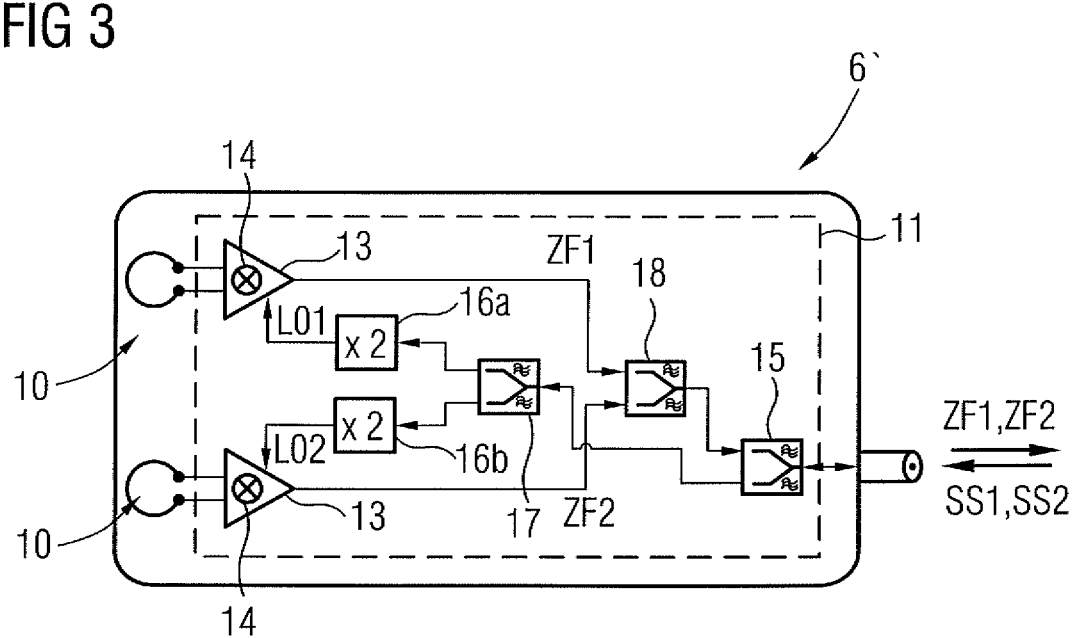
FIG. 3 shows a second exemplary embodiment of a local coil.

FIG. 3 shows an embodiment of a local coil 6' that is preferred to the embodiment in FIG. 2, with the same reference characters being used for corresponding elements to simplify the illustration. In contrast to FIG. 2, the diplexer here is configured to split the intermediate signals SS1, SS2 before frequency doubling by the frequency multipliers 16A, 16B (e.g., frequency doublers) takes place separately for the two intermediate signals. Spectral separation takes place in the low frequency position, in other words at 142.5 MHz and 152.5 MHz. Two separate frequency doublers 16A, 16B are present. Two separate frequency doublers 16A, 16B reduce the dynamic requirement for the frequency doublers 16A, 16B by 6 dB, since the double frequency signal has a 6 dB greater peak power (PEP, peak envelope power) than the respective individual intermediate signals. Interfering intermodulation products do not occur in this arrangement.

In principle, more than two receive signals may be multiplexed in the manner shown, although multiplexing more than two receive signals may be associated with a high level of complexity. A larger number of auxiliary frequency signals may also be required.

The preprocessing circuits 11 shown as incorporated in the local coil housing of the local coil 6 in FIGS. 2 and 3 can also be configured as a separate component, which can be provided for example between the coil plug and the plug-in point on the patient couch 4.

Figure 4:
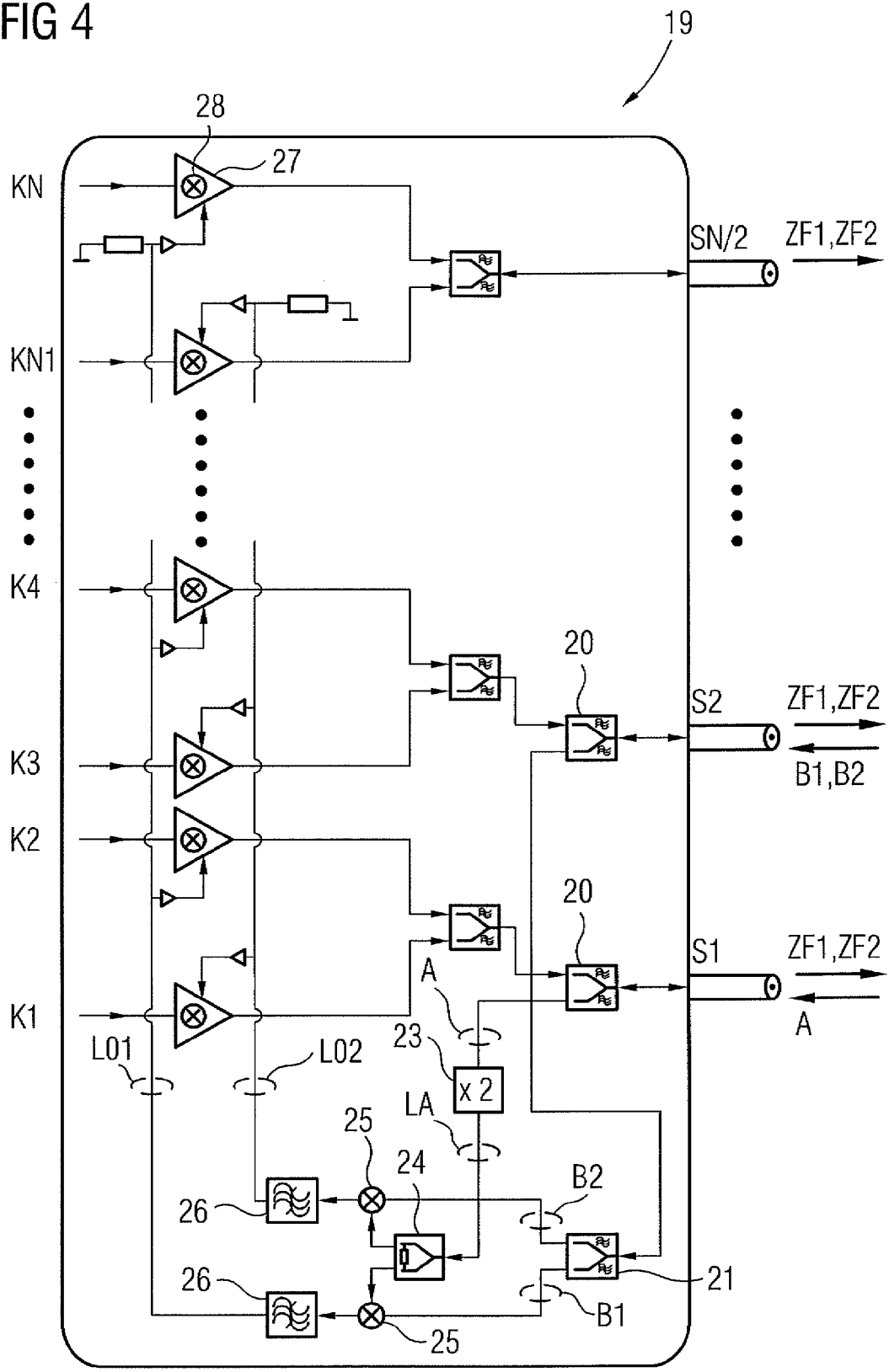
FIG. 4 shows one embodiment of a preprocessing circuit.

FIG. 4 shows a further embodiment in the form of a preprocessing circuit 19 for a local coil with N transmit channels K1-KN. The corresponding signal inputs are shown schematically on the left side of FIG. 4. Provision is also made for combining two of the receive channels in each instance, transforming the receive signals to different intermediate frequencies ZF1, ZF2 and transmitting the intermediate frequency signals using a multiplex procedure by a shared cable to the receive system 9, so that only N/2 transmission links are required, as shown on the right in FIG. 4.

The exemplary embodiment in FIG. 4 also indicates a possibility for implementing in a system. For reasons of frequency planning, a prerequisite excludes the selection of intermediate signal frequencies and auxiliary signal frequencies which are not whole-number multiples of 5 MHz, for example.

In the exemplary embodiment in FIG. 4, to generate two auxiliary frequency signals LO1, LO2 with auxiliary frequencies of 285 MHz and 305 MHz, two transmitted auxiliary frequency signals and one intermediate signal are used. For example, an intermediate signal A is at 85 MHz. The intermediate signal A is supplied by way of the second transmission link S1 assigned to the channels K1 and K2, and the auxiliary frequency signal pair B1 and B2 at 115 MHz and 135 MHz reaches the preprocessing circuit 19 by way of the transmission link S2 assigned to the channels K3 and K4. No intermediate signals or auxiliary frequency signals are transmitted by way of the remaining transmission links.

The auxiliary frequency signals LO1 and LO2 are generated from the three signals A, B1, B2. The intermediate signal A or the auxiliary frequency signals B1, B2 are first separated from the receive signals at intermediate frequency ZF1, ZF2 by a diplexer 15, as shown in FIG. 2 and FIG. 3. A further diplexer 21 follows for the auxiliary frequency signal pair B1, B2, so that the auxiliary frequency signals B1 and B2 are then present separately. In parallel, intermediate signal A is doubled by a frequency multiplier 23, in this instance a frequency doubler again, to 170 MHz to form an auxiliary frequency signal LA. The auxiliary frequency signal LA is doubled by a signal splitter 24 and supplied in each instance as an input signal to a mixer 25. The other input of the mixer 25 is supplied with the signal B1 or B2. The resulting auxiliary frequency signals LO1 and LO2 are selected by way of filter 26 and are then available in the system at the frequencies 285 MHz and 305 MHz.

The synthesizer auxiliary frequency signal pair B1, B2 is therefore broken down, initially spectrally, into two components before the individual auxiliary frequency signals B1, B2 are each passed to a mixer 25. The spectral separation of the signal pair B1, B2 at (here) 125 MHz center frequency may be technically simpler than an (alternative) spectral separation of the auxiliary frequency signal pair LO1 and LO2 at a center frequency of 295 MHz, since there is a greater relative frequency gap due to the frequency gap of 20 MHz that advantageously remains the same here at the lower frequencies. The dynamic requirement for the mixers 25 is also reduced by 6 dB here as in the exemplary embodiment in FIG. 3.

Once available, the auxiliary frequency signals LO1 and LO2 are then supplied correspondingly to the modules 27 with the mixers 28 for the respective channels to generate the intermediate frequencies ZF1 and ZF2.

In the exemplary embodiment illustrated in FIG. 4, the intermediate and auxiliary frequency signals are all located in a predefined 5 MHz grid. The illustrated concept of generating two auxiliary frequency signals from two auxiliary frequency signals and one intermediate signal may also be applied independently of such a grid. The preprocessing circuit 19 may also be a fixed part of a local coil.

In the exemplary embodiments, the illustrated frequency multipliers 16, 16A, 16B, 23 are implemented as diode multipliers, in other words passive frequency multipliers.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A preprocessing circuit for receive signals of a local coil in a magnetic resonance facility, the preprocessing circuit comprising:
    a wired transmission link operable to transmit a receive signal and an intermediate signal;
    a frequency multiplier arranged to generate an auxiliary frequency signal of an auxiliary frequency from the intermediate signal transmitted from a receive system of the magnetic resonance facility via the wired transmission link, the intermediate signal having a frequency corresponding to a whole-number fraction of the auxiliary frequency.

2. The preprocessing circuit of claim 1, wherein the wired transmission link is a single wired transmission link.

3. The preprocessing circuit of claim 2, further comprising a multiplexer downstream or upstream of the frequency multiplier, the multiplexer configured to separate auxiliary frequency signals or intermediate signals.

4. The preprocessing circuit of claim 2, further comprising a multiplexer connected upstream of the frequency multiplier to separate the intermediate signal from the receive signal.

5. The preprocessing circuit of claim 4, further comprising at least one mixer operable for generating the auxiliary frequency signal by mixing, the at least one mixer connected with the frequency multiplier.

6. The preprocessing circuit of claim 4, wherein the multiplexer comprises a diplexer.

7. The preprocessing circuit of claim 1, further comprising a multiplexer downstream or upstream of the frequency multiplier, the multiplexer configured to separate auxiliary frequency signals or intermediate signals.

8. The preprocessing circuit of claim 7, further comprising at least one mixer configured to transform the receive signal to a low intermediate frequency using the auxiliary frequency.

9. The preprocessing circuit of claim 1, further comprising at least one mixer operable for generating the auxiliary frequency signal by mixing, the at least one mixer connected with the frequency multiplier.

10. The preprocessing circuit of claim 1, further comprising at least one mixer configured to transform the receive signal to a low intermediate frequency using the auxiliary frequency.

11. The preprocessing circuit of claim 1, wherein the frequency multiplier is a passive frequency multiplier.

12. The preprocessing circuit of claim 11, wherein the passive frequency multiplier comprises a diode multiplier.

13. The preprocessing circuit of claim 1, wherein the frequency multiplier comprises a frequency doubler.

14. The preprocessing circuit of claim 1, wherein the whole-number fraction of the auxiliary frequency comprises half the auxiliary frequency.

15. The preprocessing circuit of claim 1, wherein the preprocessing circuit is configured to supply all auxiliary frequency signals.

16. A local coil comprising:
a wired transmission link operable to transmit a receive signal and an intermediate signal;
a frequency multiplier arranged to generate an auxiliary frequency signal of an auxiliary frequency from the intermediate signal transmitted from a receive system of a magnetic resonance facility via the wired transmission link, the intermediate signal having a frequency corresponding to a whole-number fraction of the auxiliary frequency.

17. A method for supplying at least one auxiliary frequency signal of an auxiliary frequency at a preprocessing circuit for receive signals assigned to a local coil for a magnetic resonance facility, the method comprising:
transmitting on a wired transmission link from a receive system an intermediate signal with a frequency corresponding to a whole-number fraction of the at least one auxiliary frequency signal;
transmitting on the wired transmission link at least one receive signal; and
generating the at least one auxiliary frequency signal from the intermediate signal with a frequency multiplier.

18. The method of claim 17, wherein the transmitting on the wired transmission link is performed for all auxiliary frequency signals.

19. The method of claim 17, further comprising generating the intermediate signal in the receive system.

20. The method of claim 17, further comprising splitting different signals transmitted by the wired transmission link.

21. The method of claim 20, further comprising transmitting a plurality of intermediate signals for generating a plurality of auxiliary frequency signals;
wherein the plurality of intermediate signals are split before the frequency is increased.

22. The method of claim 17, further comprising generating at least one further auxiliary frequency signal by mixing at least one auxiliary frequency signal with another auxiliary frequency signal.

* * * * *